United States Patent [19]

Bauernfeind

[11] Patent Number: 4,483,728

[45] Date of Patent: Nov. 20, 1984

[54] RELIEVED PATTERNED MARRYING ROLL

[75] Inventor: Robert N. Bauernfeind, Appleton, Wis.

[73] Assignee: Kimberly-Clark Corporation, Neenah, Wis.

[21] Appl. No.: 168,748

[22] Filed: Jul. 14, 1980

[51] Int. Cl.³ .................. B32B 29/02; B32B 31/08
[52] U.S. Cl. .................. 156/209; 156/292; 156/324; 156/553; 156/582; 428/154; 428/166; 428/172
[58] Field of Search .............. 428/153, 154, 166, 178, 428/180, 172; 156/209, 324, 292, 553, 555, 582

[56] References Cited

U.S. PATENT DOCUMENTS

| | | | |
|---|---|---|---|
| 3,414,459 | 12/1968 | Wells | 156/209 |
| 3,694,300 | 9/1972 | Small | 156/209 |
| 3,738,905 | 6/1973 | Thomas | 428/154 |
| 3,867,225 | 2/1975 | Nystrand | 428/180 |

Primary Examiner—Paul J. Thibodeau
Attorney, Agent, or Firm—Gregory E. Croft

[57] ABSTRACT

A patterned marrying roll especially adapted to combined multiple plies of a tissue sheet at a nip between the marrying roll and an embossing roll. The marrying roll is provided with a pattern of raised laminating elements covering a predetermined percentage of the marrying roll surface which are caused to bear against the raised embossing elements of an embossing roll with the plies of a pillowed tissue sheet therebetween. The pattern of raised elements on the marrying roll surface may be in the form of dots, a recticular grid pattern, or any other pattern of choice. The pattern is preferably aligned at an angle to the machine direction to eliminate bunching or puckering of the tissue sheet between pattern elements. The pattern on the marrying roll may comprise from approximately 10% to approximately 40% of the marrying roll surface. The invention is intended primarily for use in laminating plies of a "pillowed" cellulose sheet together, but may also be advantageously used in the lamination of "nested" sheet plies.

6 Claims, 9 Drawing Figures

RELIEVED PATTERNED MARRYING ROLL

BACKGROUND OF THE INVENTION

Multiple ply laminated embossed paper products are typically of two types, "nested" and "pillowed", each of which has substantially greater bulk than nonembossed multiple ply products. When a tissue or towel sheet is provided with an embossed pattern, projecting land areas and recessed areas are produced corresponding to the land areas and recessed areas of the embossing roll. A "nested" product results when projecting land areas of a first web are aligned in the recessed areas between two land areas of a second web, whereas a "pillowed" sheet results when the projecting land areas of both first and second webs are placed adjacent one another with the recessed areas of the two sheets creating a relatively large void between adjacent land areas.

The primary problem associated with multi-ply embossed paper webs is that, traditionally, the plies have been combined at the nip between the two steel embossing rolls. This metal-to-metal contact at the embossing roll nip has resulted in excessive wear on the embossing rolls requiring frequent and costly repairs or replacements. This problem was recognized in U.S. Pat. No. 3,867,225, Nystrand, wherein the plies are combined between one of the steel embossing rolls and a rubber covered "marrying roll", which permits the nip between the two embossing rolls to be run open, reducing wear on and extending greatly the useful life of the embossing rolls.

However, the process of the Nystrand patent is useful only for producing a "nested" type product, since the solid surface marrying roll would substantially debulk a pillowed product. A pillowed multi-ply product is shown in U.S. Pat. No. 3,738,905, Thomas, however this method suffers from the aforementioned embossing roll wear problem at the combiner nip. A solid surface marrying roll as disclosed in the Nystrand patent utilized with this process would result in approximately 50% of the laminated sheet bulk being removed during the embossing stage. Therefore, there is a need for an embossing roll which will permit the embossing of pillowed as well as nested multi-ply webs without debulking the web to any appreciable extent.

SUMMARY OF THE INVENTION

In the present invention, there is a method described for producing a multi ply soft absorbent tissue sheet, the tissue sheet comprising first and second embossed tissue webs which are combined at the nip between an embossing roll and a patterned marrying roll. Adhesive is applied to one of the tissue sheets so that the combination of the adhesive and pressure from the combiner nip laminates the tissue webs to one another in the pattern provided on the marrying roll. The pattern on the marrying roll may comprise raised elements of any design of choice, such as a cross hatched grid design or a series of dots. Preferably, the design on the marrying roll is arranged at an angle to the machine direction of the tissue webs. The raised elements of the marrying roll design may comprise from about 10% to about 40% of the surface area of the marrying roll. The lamination of the tissue sheet occurs only at those points where raised land areas of the two embossed webs intersect and are combined by the patterned elements of the marrying roll.

It has been found that by relieving the pattern on the marrying roll, such as by providing spaces in the raised elements of a cross hatched grid design, creasing of the finished product may be avoided.

The method of the present invention may be utilized with either a pillowed or a nested multi-ply cellulose web in order to combine the plies in a predetermined pattern.

DESCRIPTION OF THE PREFERRED EMBODIMENT

Figure 1:
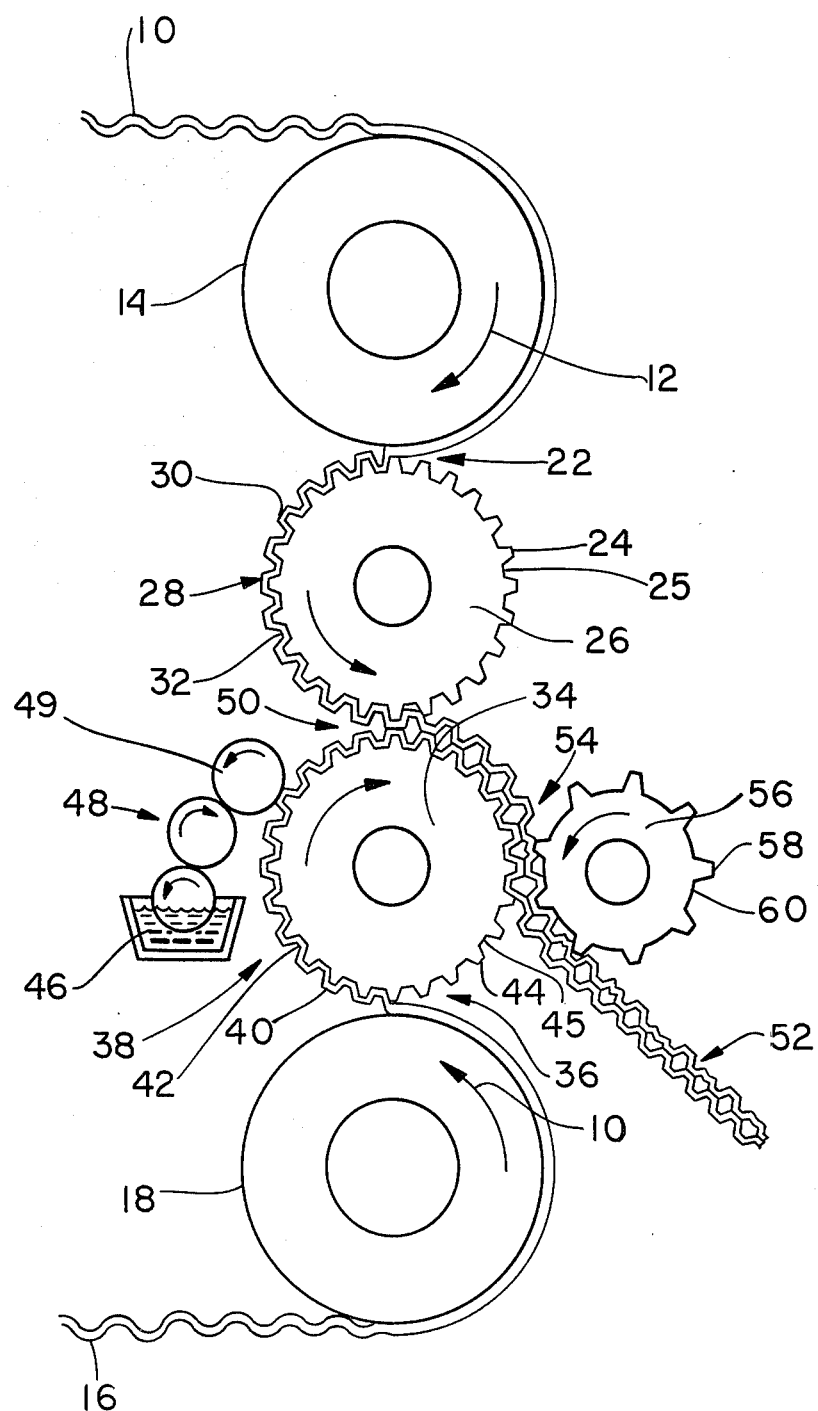
FIG. 1 is a schematic view of the apparatus of the present invention as seen from one side.

Referring now to the drawings, the numeral 10 in FIG. 1 indicates a first web of creped tissue moving around a first rubber roll 14 (or a roll covered with any other resilient covering) in the direction indicated by arrow 12. A second web of creped tissue 16 moves about a second rubber covered roll 18 in the direction of arrow 20. The web 10 is directed about roll 12 to a first embossing nip 22, wherein web 10 is embossed by the indication of upstanding land areas 24 on the first steel embossing roll 26 into the resilient covering of roll 14. The resulting first embossed web 28 is provided with upstanding land areas 30 and recessed areas 32 corresponding to land areas 24 and recessed areas 25 of embossing roll 26. (It is to be understood that the projecting land areas of one side of the first embossed web 28 would be the recessed areas of the opposing side of the web 28, and vice versa.) Likewise, the second web 16 is embossed between second steel embossing roll 34 at the second embossing nip 36, producing a second embossed web 38 having alternating projecting land areas 40 and recessed areas 42 corresponding to land areas 44 and recessed areas 45 on roll 34.

The surface of one of the embossed webs 28 or 38 is provided with a laminating adhesive 46 supplied by a flexographic type applicator generally indicated at 48, which may apply adhesive either overall or in a pattern to one of the webs. Adhesive is applied to the web only on the projecting land areas, and only in a very fine film. The embossed webs are combined at the open nip 50 between embossing rolls 26 and 34 with projecting land areas 30 and 40 being placed adjacent to one another. The adhesive applied from applicator 48 is insufficient to laminate the webs together because the nip between embossing rolls 26 and 34 is run in the open position to prevent embossing roll damage.

The partially laminated sheet 52 travels around embossing roll 34 and the webs 28 and 38 are laminated at the nip 54 between embossing roll 34 and the marrying roll 56. The marrying roll 56 is provided with projecting land areas 58 and recessed areas 60 of any desired pattern (as described in greater detail below).

Figure 2:
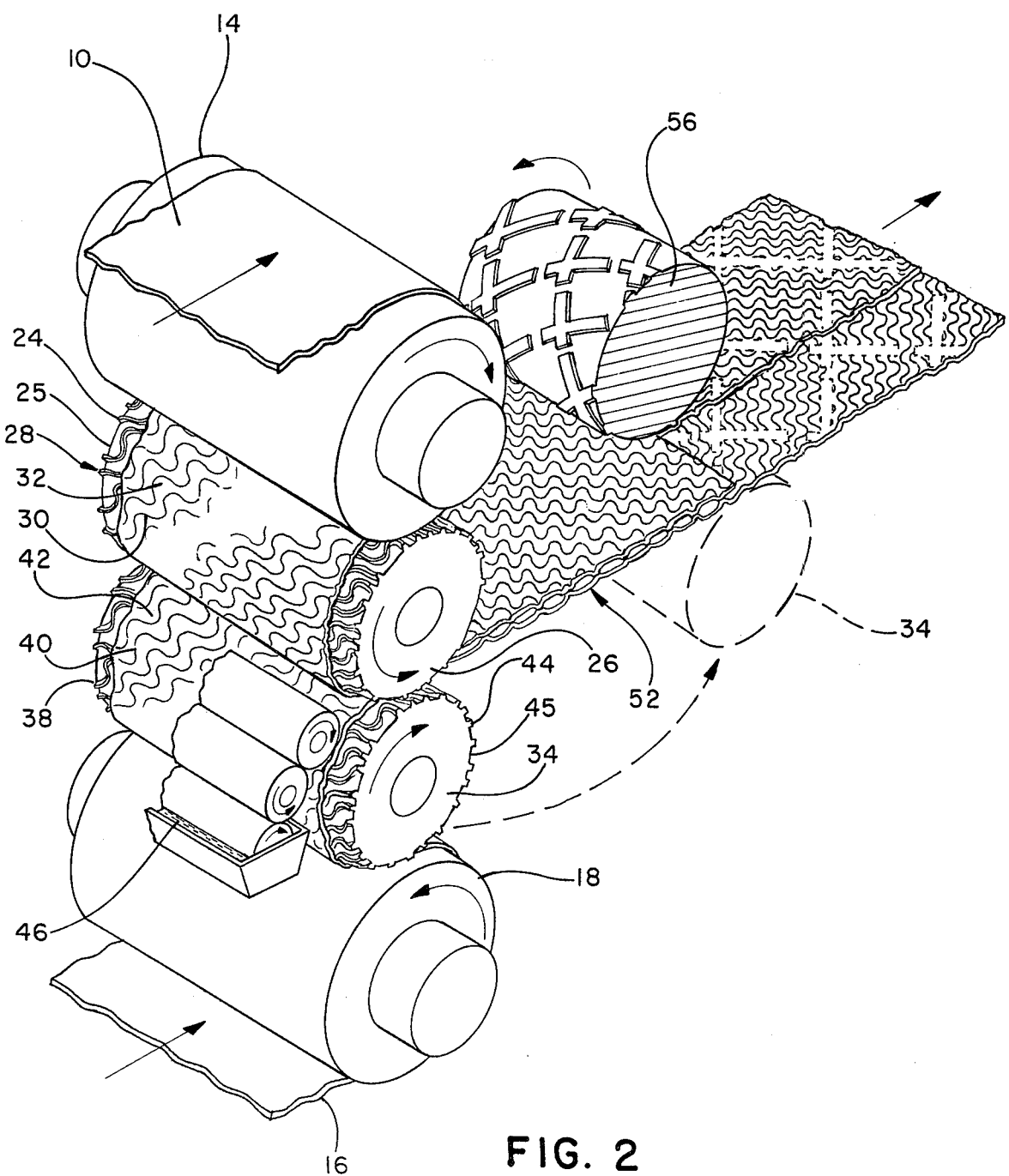
FIG. 2 is an isometric view of the invention of FIG. 1 distorted to more clearly show the present invention.

Referring now to FIG. 2, the embossing pattern of the steel embossing rolls 26 and 34 may be seen to be arranged in a "sine wave". The rolls 26, 34 rotate in opposite rotational direction so that the land areas 24, 44 of the rolls extend in crossing relation. With the adhesive 46 being applied to the land areas 40 of web 38, a small degree of adhesion between webs 28 and 38 may be achieved at the location of crossover of land areas 30,40 in sheet 52, although if the nip 50 is run in a fully open position (e.g. greater than 0.002 inch for 11-14 pound basis weight plies), no lamination will result.

The webs 28, 38 of sheet 52 are finally laminated at the marrying roll nip 54 in the pattern of the marrying roll 56. The location of the marrying roll 56 in FIG. 2 has been distorted so that the pattern applied to sheet 52 may be more easily seen. It is to be understood that roll 56 of FIG. 2 would, in operation, be aligned with its axis of rotation in approximately the same horizontal plane as roll 34. The sheet 52 moves through the nip 54 between marrying roll 56 and embossing roll 34, with embossing roll 34 being shown in broken lines in FIG. 2.

Figure 3:
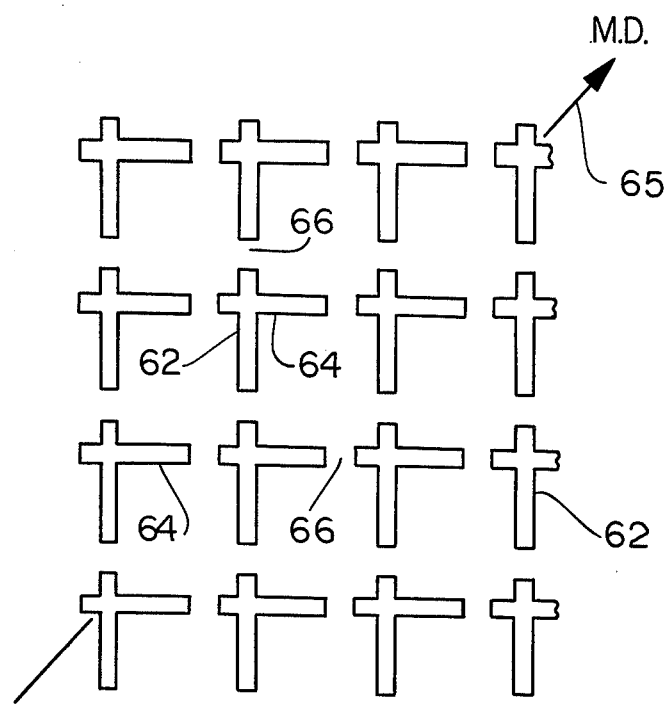
FIG. 3 is a schematic view in plan representing a pattern on the surface of a marrying roll of the present invention.
Figure 4:
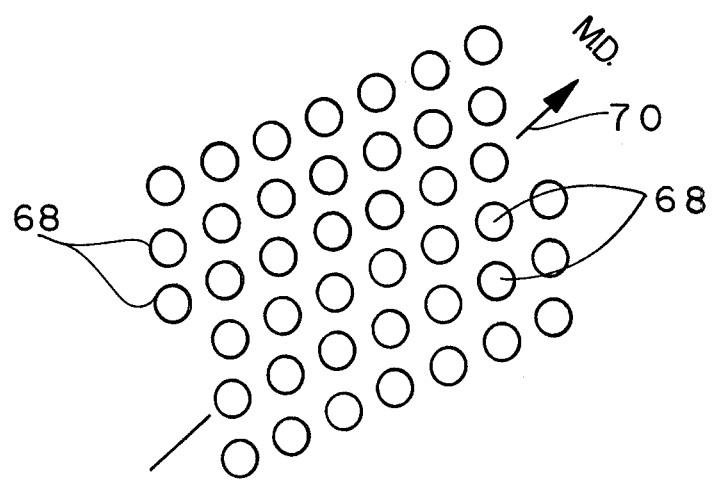
FIG. 4 is a schematic view in plan representing a second embodiment of the surface of a marrying roll of the present invention.

As shown in FIGS. 3 and 4, two possible patterns for the raised elements of the marrying roll are rectangular cross-hatch and raised dots. The pattern of FIG. 3 (shown on the marrying roll 56 of FIG. 2) comprises raised elements 62 and 64 arranged perpendicular to one another and to offset in the machine direction, as indicated by arrow 65. While the raised elements 62 and 64 could comprise a continuous cross-hatch pattern, it has been found that when so arranged, the sheet tends to "pucker" between successive raised elements arranged perpendicular to the machine direction, and produces unacceptable creases or fold lines in the finished product as it moves through the nip 54. Therefore, by arranging the pattern at an angle to the machine direction and by relieving the pattern with spaces 66 in each element between adjacent parallel elements, this undesirable creasing may be partially eliminated. Alternatively, the pattern on the marrying roll may comprise raised dots 68 arranged in staggered rows which are arranged at an angle to the machine direction as indicated by arrow 70 in FIG. 4. Because there is a substantial open area between each raised dot element on the marrying roll, there is sufficient space for the sheet to pucker slightly without causing unacceptable creasing of the web. The angle at which the pattern is arranged to the machine direction may vary depending upon basis weight, laminating pressure, machine speed, etc. Therefore, the optimal angle may be determined only by experimentation for each particular pattern or set of operating parameters.

The raised elements, whether in a grid, dot or any other pattern of choice, may comprise a percentage of the surface area of the marrying roll from 0 to 100 percent, and thereby laminate the individual plies together over a corresponding percentage of their surfaces. However, it has been found advantageous to arrange these elements such that they comprise no more than 40%, and preferably no less than 10%, of the marrying roll surface area. Based upon trials using different marrying roll surfaces, it is believed that an amount less than 10% would provide less than adequate lamination of the plies to one another, while an amount greater than 40% would debulk the resulting sheet unnecessarily without substantially increasing the quality of the sheet from the additional lamination.

Figure 5:
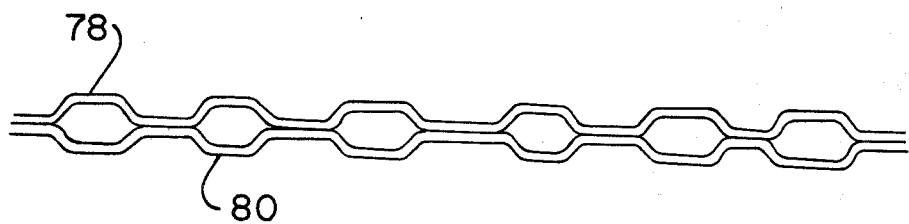
FIG. 5 is a schematic cross-sectional view of a "pillowed" cellulose web.
Figure 6:
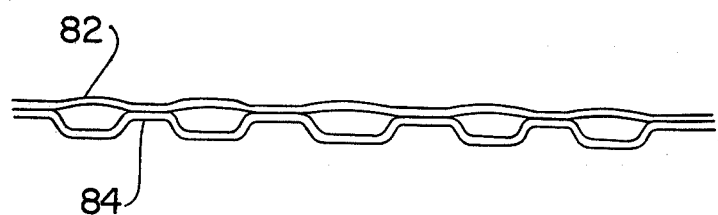
FIG. 6 is a schematic cross-sectional view of a "pillowed" cellulose web combined with a solid surface marrying roll.

FIG. 5 illustrates a typical "pillowed" tissue sheet such as is produced by the process of U.S. Pat. No. 3,738,905, wherein the web plies 78, 80 are combined and laminated at the nip between the steel embossing rolls. In order to run this nip open, thereby reducing wear and tear on the expensive embossing rolls, the plies must be laminated by a marrying roll as shown in U.S. Pat. No. 3,867,225. However, it has been known only to combine "nested" multiple ply tissue sheets by this method, since a solid surface marrying roll will not debulk a nested sheet to the same degree it will debulk a pillowed sheet. If such a solid surface marrying roll were used to combine the pillowed sheet of the present invention, the resulting sheet, illustrated diagrammatically in FIG. 6, would have a substantial portion of the original bulk of the 2 ply sheet removed by compression of the sheet between the marrying roll surface and the embossing roll. Because the solid surface marrying roll combines the plies against the embossing roll, the web 82 adjacent the marrying roll would be compressed essentially to the level of the web 84 which is molded to the projecting elements of the embossing roll.

Figure 7:
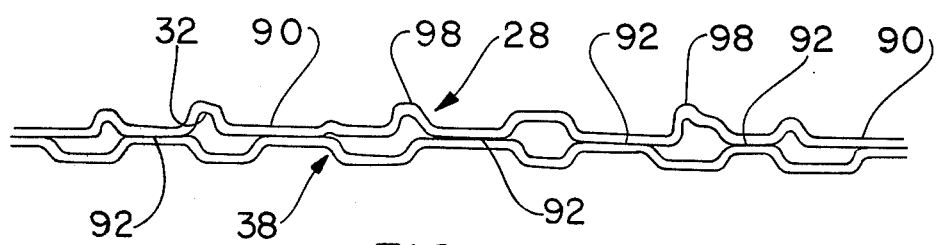
FIG. 7 is a schematic cross-sectional view of a cellulose web made according to the present invention.

By contrast, a diagrammatic cross-section of a sheet produced by the apparatus and process of the present invention, as shown in FIG. 7, retains a substantial portion of its original bulk even though it is debulked to a certain extent by the marrying roll. The "lower" ply 38 follows the embossing roll 34 as shown in FIG. 1, and is not compressed by the marrying roll 56. The "upper" ply 28 adjacent the marrying roll 56 is compressed to some extent by the marrying roll, the amount of compression depending upon the percentage of the surface area of the marrying roll covered by the raised elements thereon. As shown in FIG. 7, the plies 28 and 38 are laminated only at those places where the land areas 30, 40 of the plies 28 and 38, and the embossing pattern of the marrying roll elements 58, intersect. For instance, plies 28 and 38 intersect at 90 in FIG. 7, and have been laminated at that point by an element of the marrying roll 56. The recessed areas 32 of web 28 have been partially debulked during this lamination.

The lamination of the plies 28 and 38 to one another is effected only at the intersection of raised elements 58 of the marrying roll and the land areas 44 of the embossing roll 34, as indicated by the numeral 90 in FIG. 7, while the intersecting points designated 92 in FIG. 7 are adhered together only by the adhesive application on web 38. The number of areas of compression 90 may be varied depending upon that portion of the surface area of the sheet which is considered necessary to effect sufficient lamination for adequate sheet performance. Of course, it would in most instances be preferable to have as little lamination as possible, since the compressed areas 90 have considerably less bulk and absorbency than the rest of the sheet.

Figure 8:
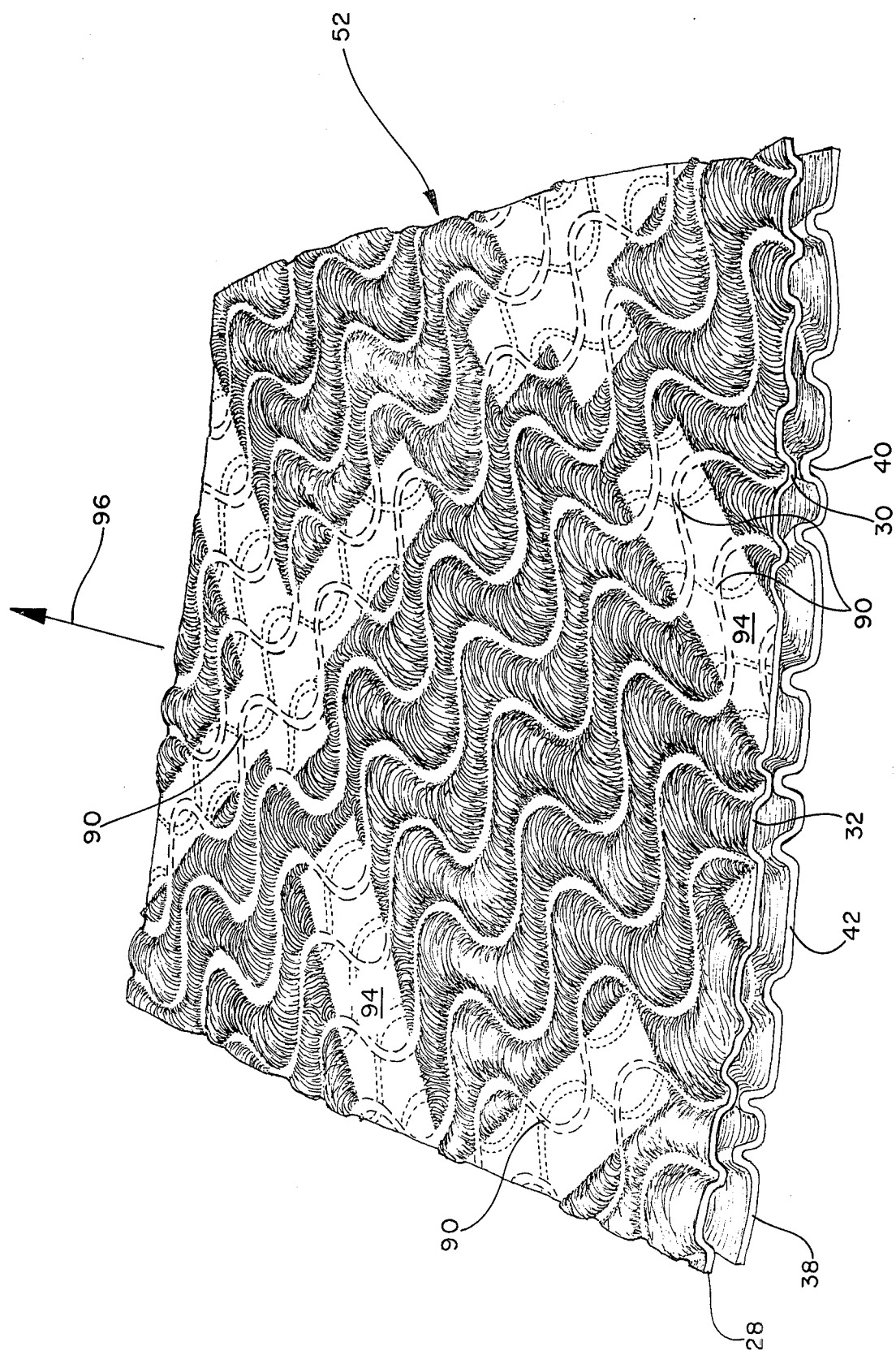
FIG. 8 is a fragmentary perspective view of a cellulose web made according to the present invention.

A somewhat more comprehensible view of this effect is seen in FIG. 8. The "sine wave" pattern produced by the embossing rolls 26, 34 of FIGS. 1 and 2 may be seen in the plies 28 and 38 of sheet 52. The recessed areas 32 and 42 of plies 28 and 38 respectively form the "pillow" which gives bulk to the sheet and gives the sheet its appealing characteristics. At those points where the land areas 30,40 intersect, if adhesive was applied to that point on web 38, some lamination of the plies may result. However, without lamination by the marrying roll, this adhesion is minimal and probably insufficient to cause the two plies to effectively adhere to one another.

Figure 9:
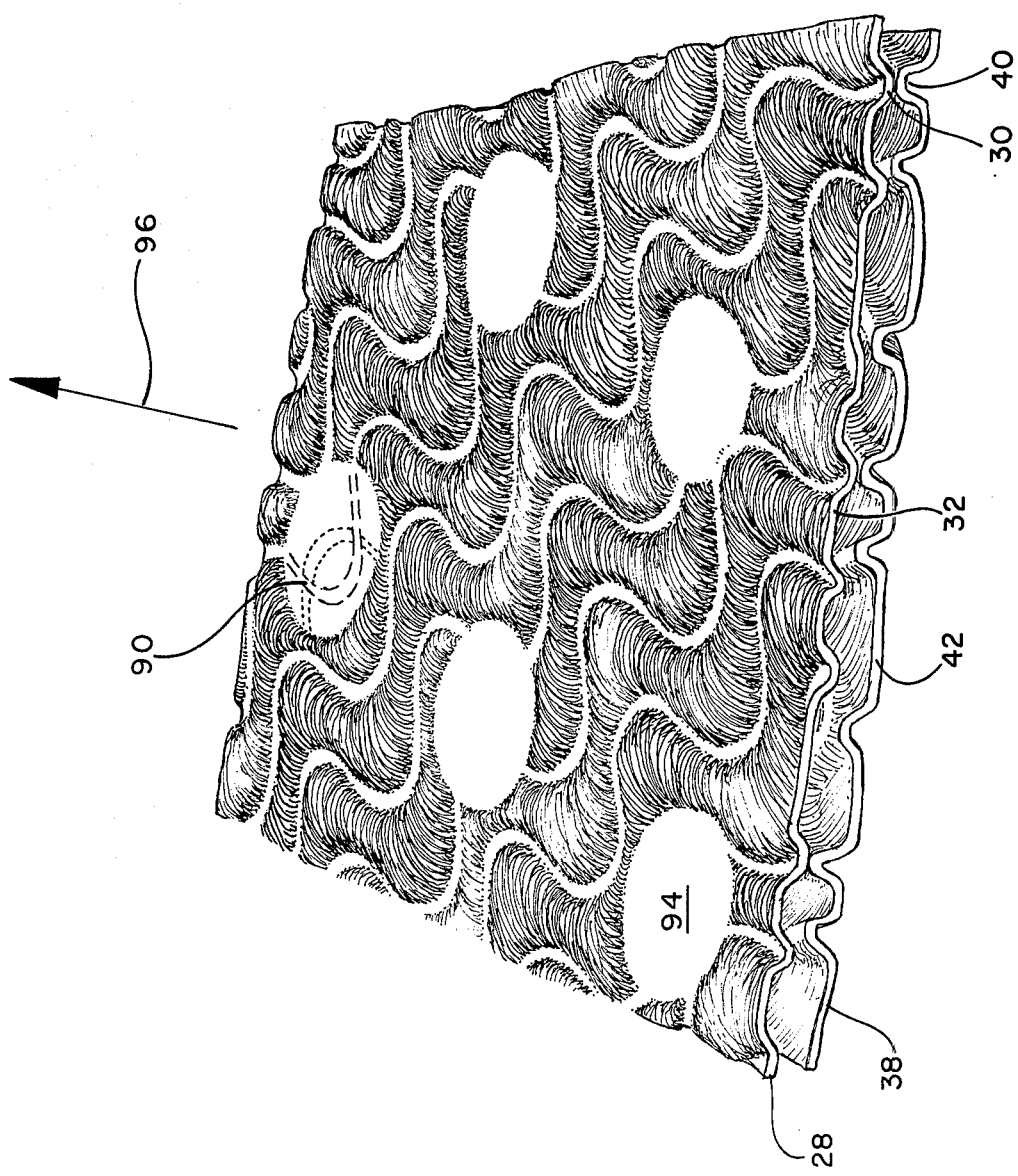
FIG. 9 is a fragmentary perspective view of an alternative embodiment of a cellulose web made according to the present invention.

However, in the area of the embossment 94 of an element of the marrying roll 56, and especially at those points designated 90, lamination is complete between the two plies if adhesive is present on land area 40 of ply 38. If adhesive is applied to ply 38 by a solid surface printing roll 49, all points of crossover 90 imprinted by marrying roll elements 58 will be laminated. However, if a patterned roll 49 is used, only a portion of sites 90 will result in lamination. As is readily apparent, the sheet 52 of FIG. 8 has the beneficial aspects of a pillowed sheet (especially bulk) and yet is laminated with a minimal amount of compressed areas. By arranging the marrying roll pattern at an angle to the machine direction (indicated by arrow 94) and by relieving the pattern on the marrying roll, creasing of the sheet is greatly alleviated. FIG. 9 is a three-dimensional representation of the marrying roll pattern of FIG. 4, indicating the points of lamination as in FIG. 8.

A somewhat unexpected result of practicing the present invention is shown in FIG. 7. Obviously, using a marrying roll, patterned or solid surfaced, will debulk the embossed sheet to a greater or lesser extent. When using a patterned marrying roll of the present invention having a raised embossing area of, for instance, 30%, one would expect a 30% loss of bulk in the resultant sheet. It has been observed, however, that the debulking resulting from the patterned marrying roll is something less than 30%, on the order of approximately 25%. It is believed that as a result of the nip between the marrying roll 56 and the embossing roll 34, the web 28 is caused to pucker slightly, although not to the extent of causing a crease. This puckering, indicated by numeral 98 in FIG. 7, actually increases the bulk of the sheet from that which would be expected based upon the surface embossing area of the marrying roll. While the patterned marrying roll will not increase the bulk of an embossed laminated sheet, it will cause debulking to a lesser extent than would be expected.

The process and apparatus of the present invention, while finding its primary applicability in laminating a pillowed multi-ply sheet, may also be utilized in laminating a nested multi-ply sheet. Because a nested sheet has a protruding land area of a first web "nested" within the recessed area of a second web, to which it is to be laminated, it does not usually have the pillowed sheet, the laminated sheet being somewhat thicker than the thickness of one web (whereas a pillowed sheet is approximately twice as thick as an individual web). Whereas a solid marrying roll would laminate every potential laminating point, as shown in U.S. Pat. No. 3,867,225, the use of a patterned marrying roll, as in the present invention, would preferentially laminate only a predetermined portion of the sites available. This patterned lamination will result in a sheet having greater drape (limpness) characteristics, and therefore greater consumer appeal.

It is to be understood that the invention is not to be limited to the specific constructions, arrangements and devices shown and described, except only insofar as the claims may be so limited, as it will be understood to those skilled in the art that changes may be made without departing from the principles of the invention.

What is claimed is:

1. A method of producing a multi-ply soft absorbent cellulose web comprising the steps of:
   (a) embossing first and second separate tissue webs on first and second embossing rolls, said embossing rolls having a pattern of raised embossing areas thereon such that a repeating pattern of projecting land areas and recessed areas is produced on each tissue web;
   (b) applying adhesive to said projecting land areas of one of said tissue webs;
   (c) aligning said separate tissue webs such that a portion of said projecting land areas of said first tissue web are in contact with a portion of said projecting land areas of said second tissue web, with said recessed areas of said separate tissue webs being spaced apart from one another; and
   (d) combining said first and second tissue webs at the location of a combiner nip formed between one of said embossing rolls and a relieved patterned marrying roll, said marrying roll having a discrete pattern of raised surfaces thereon, whereby, said first and second tissue webs are laminated one to another at the locations where said raised surfaces of said marrying roll contact said points of contact of said projecting land areas of said first and second tissue webs at said combiner nip and said resulting cellulose web is debulked only at said pattern of raised surfaces on said marrying roll.

2. The method as recited in claim 1, wherein said marrying roll comprises a substantially non-resilient rubber covered steel roll mounted adjacent one of said embossing rolls and laminating said tissue webs one to another with a pressure of at least 10 pounds per lineal inch.

3. The method as recited in claim 1, further comprising arranging said pattern on said marrying roll in the form of a repeating crosshatch grid comprising from about 10% to about 40% of said marrying roll surface, said pattern having parallel sets of raised elements arranged perpendicular to one another, such that the debulked areas of said tissue web comprise from about 10% to about 40% of the surface area of said cellulose web, and said tissue webs are laminated to one another at from about 10% to about 40% of said points of contact of said projecting land areas of said first and second tissue webs.

4. The method as recited in claim 3, further comprising arranging said pattern on said marrying roll such that said parallel sets of raised elements arranged perpendicular to one another are each arranged at an acute angle to the machine direction of said cellulose web.

5. The method as recited in claim 4, further comprising relieving said crosshatch grid pattern by providing spaces in each of said raised elements between each of said perpendicularly oriented raised elements.

6. The method as recited in claim 1, further comprising arranging said pattern in the form of raised dots of circular or rectangular configuration which cover from about 10% to about 40% of said marrying roll surface, such that the debulked area of said tissue web comprises from about 10% to about 40% of the surface area of said tissue web, and said tissue webs are laminated to one another at from about 10% to about 40% of said points of contact of said projecting land areas of said first and second tissue webs.

* * * * *

UNITED STATES PATENT OFFICE
CERTIFICATE OF CORRECTION

PATENT NO. : 4,483,728
DATED : Nov. 20, 1984
INVENTOR(S) : Bauernfeind

It is certified that error appears in the above-identified patent and that said Letters Patent are hereby corrected as shown below:

Column 2, line 44, please delete --indication-- and insert --indentation--.

Column 3, line 31, please delete --rectangular-- and insert --recticular--.

Signed and Sealed this

Sixteenth Day of April 1985

[SEAL]

Attest:

DONALD J. QUIGG

Attesting Officer    Acting Commissioner of Patents and Trademarks